United States Patent [19]

Vuillermoz et al.

[11] Patent Number: 5,344,122

[45] Date of Patent: Sep. 6, 1994

[54] TUBULAR ROD AND DEVICE FOR SAMPLING AND ANALYZING FUMES AND APPARATUS INCLUDING SUCH DEVICE

[75] Inventors: Jean-Claude Vuillermoz, Versailles; Nicolas Perrin, Louveciennes; Michel Devaux, Magny les Hameaux, all of France

[73] Assignee: L'Air Liquide, Societe Anonyme pour l'Etude et l'Exploitation des Procedes Georges Claude, Paris, France

[21] Appl. No.: 930,381

[22] PCT Filed: Dec. 31, 1991

[86] PCT No.: PCT/FR91/01084

§ 371 Date: Sep. 8, 1992

§ 102(e) Date: Sep. 8, 1992

[87] PCT Pub. No.: WO92/13108

PCT Pub. Date: Aug. 6, 1992

[30] Foreign Application Priority Data

Jan. 15, 1991 [FR] France .................. 91 00340

[51] Int. Cl.⁵ .............................................. C21C 5/52
[52] U.S. Cl. ..................................... 266/79; 266/80
[58] Field of Search .......................... 266/79, 80, 81

[56] References Cited

FOREIGN PATENT DOCUMENTS

| | | |
|---|---|---|
| 0183284 | 6/1986 | European Pat. Off. . |
| 1936649 | 2/1970 | Fed. Rep. of Germany . |
| 2328777 | 5/1977 | France . |
| 2431546 | 2/1980 | France . |
| 0983496 | 12/1982 | U.S.S.R. .................. 266/79 |
| 1370658 | 10/1974 | United Kingdom . |

OTHER PUBLICATIONS

Patent Abstracts of Japan, vol. 11, No. 268, Apr. 4, 1987, 62-74020, Mitsubishi.

*Primary Examiner*—Scott Kastler
*Attorney, Agent, or Firm*—Curtis, Morris & Safford

[57] ABSTRACT

The tubular rod (7) for sampling, mounted in a duct for the evacuation of fumes for example from a heat treatment or a melting furnace, includes an extractor tube (8) extending in a closed sleeve (9) comprising an inlet (11) and an outlet (12) of cooling fluid, the extractor tube having an end part opening outside the sleeve by means of an opening (10) for sampling fumes and a connecting part (14) extending outside the sleeve for connection to a circuit of analysis including a suction pump. The opening (10) is advantageously directed in counter-current with respect to the direction of circulation (F) of the fumes (11). Application such as for process control in an electrical furnace for the production of steel with injection of oxygenated gas.

21 Claims, 5 Drawing Sheets

TUBULAR ROD AND DEVICE FOR SAMPLING AND ANALYZING FUMES AND APPARATUS INCLUDING SUCH DEVICE

The present invention concerns devices for sampling and analyzing fumes and more particularly, it relates to a tubular rod for sampling fumes in a duct for the evacuation of fumes, typically at the outlet of a furnace for the treatment of materials, such as in metallurgy.

A device and a tubular rod of this type are described in the document GB-A-1,370.658.

The reliability of such a device depends largely on the mechanical resistance as well as the resistance to plugging due to the dusts which are present in the fumes of the sampling rod. As a matter of fact, in particular with metallurgical furnaces, the sampling of the fumes is carried out in a gas flow whose temperature varies, during one cycle, by a multiple of ten minutes in metallurgy, between room temperature and very high levels, sometimes higher than 1600° C. Moreover, the sampled fumes are extremely loaded with metallic dusts, at rates which can reach 250 g per $Nm^3$, as well as water (up to 20% in certain applications). For these reasons, presently, no device for the continuous analysis of fumes is available on the market in spite of their immediate interest for the study and optimization of the effects on the environment of emission of fumes, to provide a better knowledge of the process which generates fumes, while enabling its optimization, and making it possible to control process parameters as a function of the analysis, such as the injection of post-combustion oxygen in arc furnaces for the production of steel or ferro-alloys.

It is a first object of the invention to propose a construction of sampling tubular rod of simple and strong design, having a long life span and a limited susceptibility to plugging.

For this purpose, according to a characteristic of the invention, the tubular rod includes an extractor tube extending in a closed sleeve having a main part provided with an axis and comprising an inlet and outlet for cooling fluid, the extractor tube having an end part leading through an opening outside the sleeve and a connecting part extending outside the main part of the sleeve, at least the connecting part being typically coaxial with respect to the axis of the main part of the sleeve.

It is another object of the present invention to provide a device for sampling and analyzing fumes of increased reliability incorporating such a sampling tubular rod.

According to a characteristic of the invention, such a device for sampling and analyzing fumes in an exhaust duct for fumes defining a fumes trajectory, includes at least one tubular rod as defined above, mounted on the duct, with the opening leading into the trajectory of the fumes, the device typically including at least a suction means connected to the extractor tube of the tubular rod and to a system of analysis.

It is another object of the present invention to provide an apparatus for the production of steel or ferro-alloys enabling an optimized control of the production process.

For this purpose, according to a characteristic of the invention, such an apparatus comprises an arc furnace provided with a duct for the exhaust of fumes, and a device for sampling and analyzing fumes such as defined above, and typically means for injecting oxygenated gas into the furnace and adjustable means for feeding oxygenated gas associated with the analyzing device.

BRIEF DESCRIPTION OF THE DRAWINGS

Other characteristics and advantages of the invention will appear from the description which follows of embodiments, given by way of illustration but without limitation, with reference to the annexed drawings, in which:

In the description which follows and on the drawings, identical or similar elements will be referred to by the same reference numerals.

FIG. 1 shows an arc furnace 1 including a vat surmounted by a vault 3 carrying electrodes 4 and a duct section 5 for the exhaust fumes connected to a duct for the transfer of fumes 6 in which the fumes circulate in the direction indicated by arrow F. The furnace contains a lance for the injection of oxygen 51 and an oxycombustible burner 52.

Figure 1:
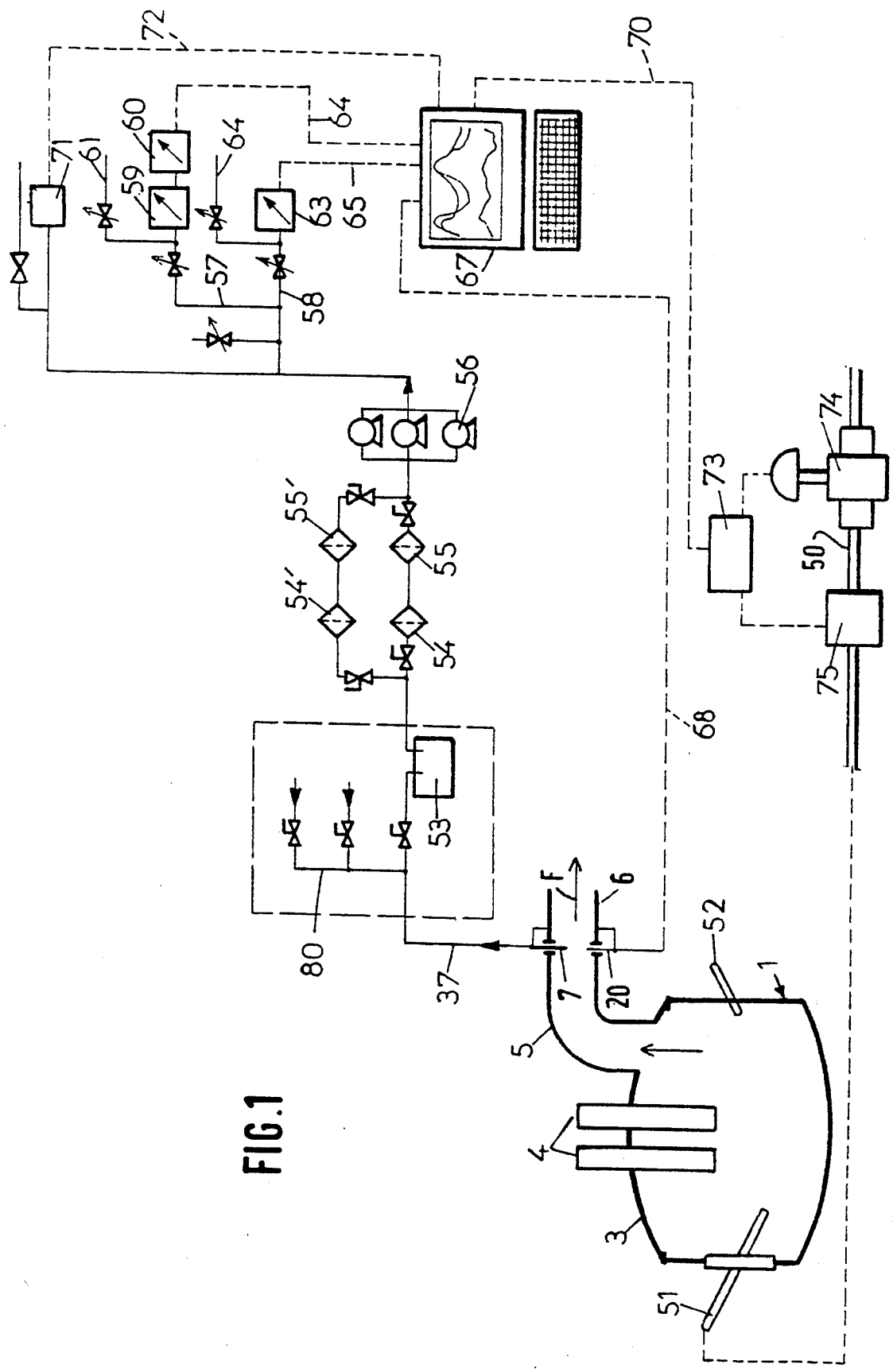
FIG. 1 is a schematic illustration of an apparatus for the production of steel or ferro-alloys according to the invention.

According to an aspect of the invention, in duct 6 there is provided a tubular rod for sampling fumes 7, connected, as will be seen more in detail latter, to a pumping group 56 forcing the drawn fumes towards analyzers 59, 60, 63.

As illustrated in FIGS. 2 to 7, a tubular rod for sampling fumes according to the invention essentially comprises an extractor tube for fumes 8 extending in a closed sleeve 9 and exiting from the latter through an opening 10 for catching fumes. Sleeve 9 includes an inlet 11 and an outlet 12 for cooling fluid, typically water. Sleeve 9 includes a main tubular part 13 having an axis and the extractor tube 8 includes a connecting part 14 which is coaxial with the main part 13 and extends outside the main part 13 of sleeve 9 via an impervious expansion joint 15, for example of the type connection with open ring, to be connected to the analyzing device.

Figure 2:
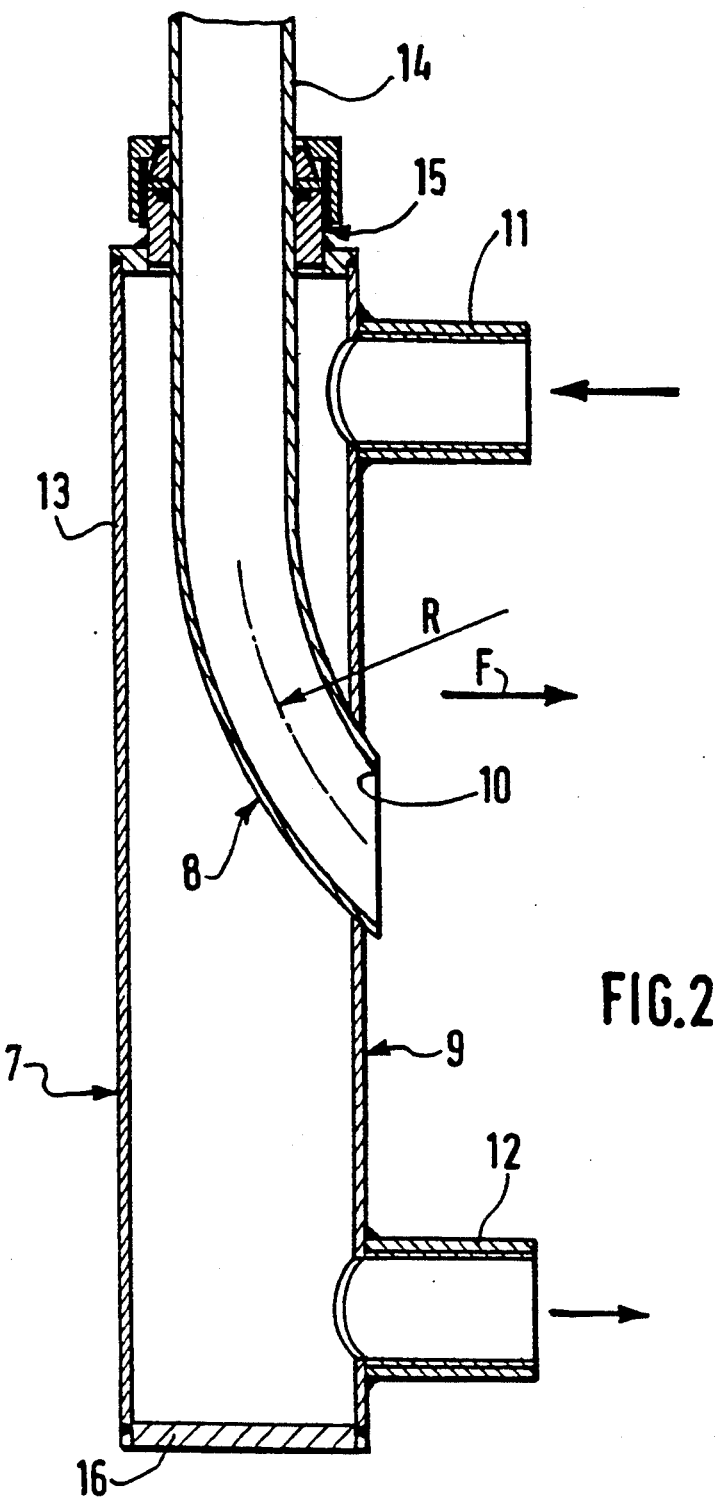
FIG. 2 is a longitudinal cross-section view of a first embodiment of a sampling tubular rod according to the invention.

In the embodiment of FIG. 2, sleeve 9 is rectilinear and closed, at the end opposite connection 15, by means of a transverse partition 16, the inlet 11 and outlet 12 of cooling fluid being laterally disposed in the vicinity of the opposite ends of the sleeve. The extractor tube 8 has an elbow shaped end part whose free end opens, flush therewith, through an orifice formed in the lateral wall of sleeve 9 by being unitary with the latter through a welding ensuring a bond between the two elements, and the imperviousness of the cooling system. To limit the risks of plugging or occlusion of the extractor tube, the elbow shaped end part of the latter has advantageously a substantial radius R, typically three times the diameter of tube 8 (for example a radius of about 85 mm for a tube 8 having a diameter of 21.3 mm corresponding to a sleeve 9 having a diameter of about 42 mm).

Figure 4:
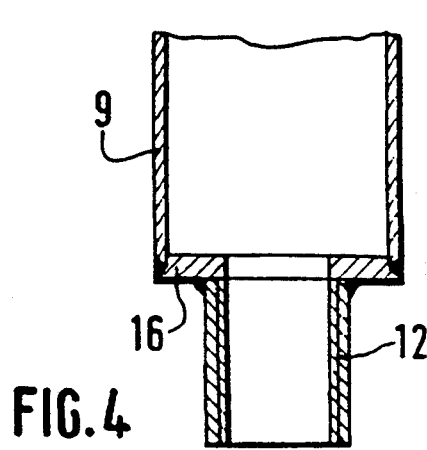
FIG. 4 is a partial view of a variant of an embodiment of the tubular rod of FIG. 2.

To limit the transverse congestion of the tubular rod 7 and facilitate for example its radial insertion into the duct for the exhaust of fumes 6, the connection of the cooling fluid outlet 12 may be coaxially mounted on the end wall 16, provided in this case with a central orifice as illustrated in FIG. 4.

Figure 5:
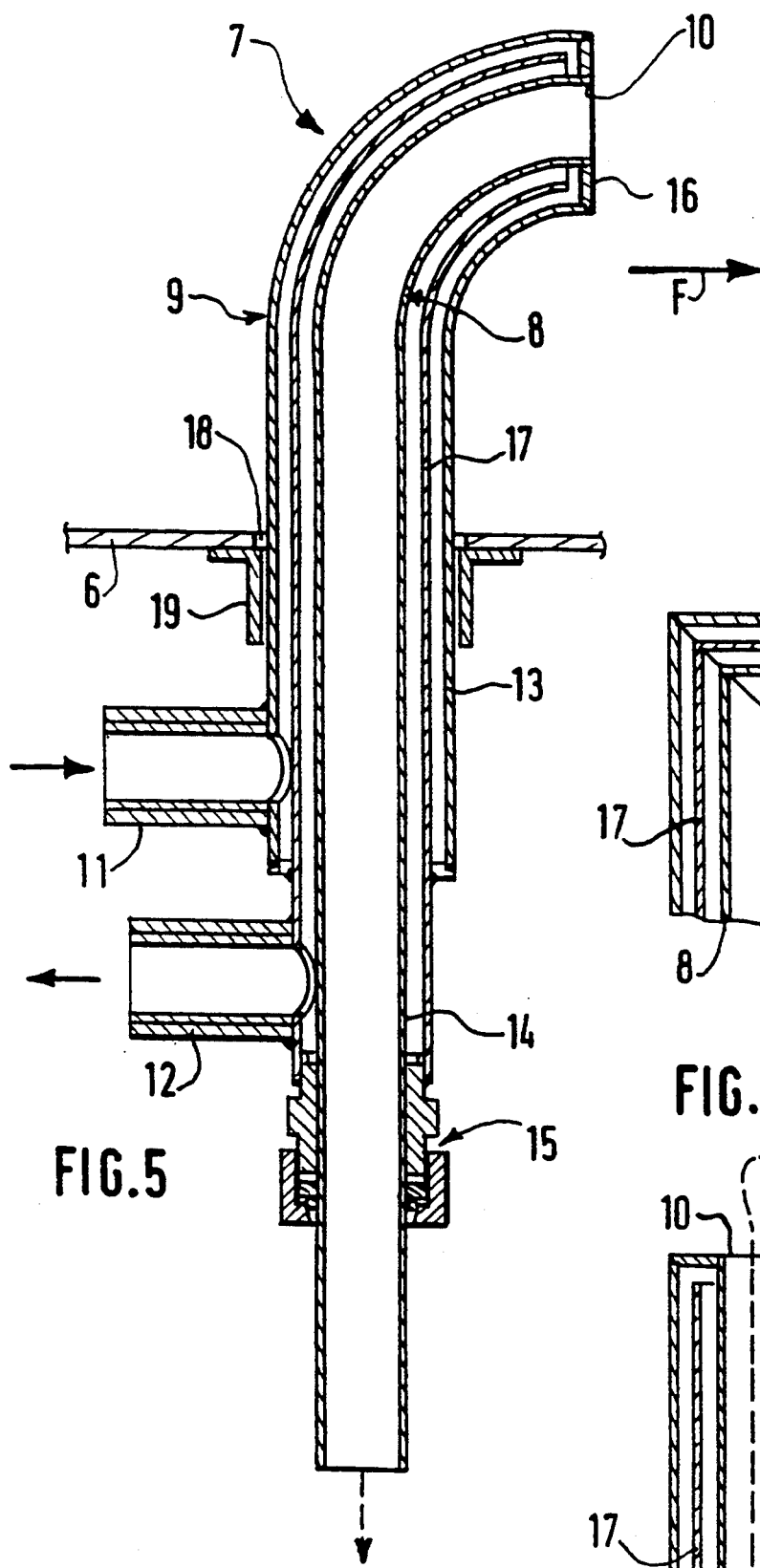
FIG. 5 is a longitudinal cross-section view of an another embodiment of a tubular rod according to the invention.
Figure 6:
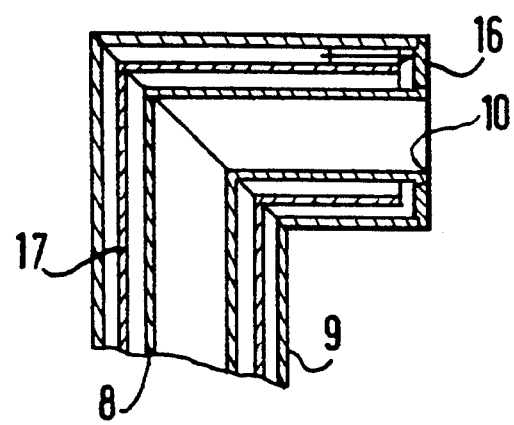
FIGS. 6 and 7 are partial view, in cross-section, of variants of the tubular rod of FIG. 5.
Figure 7:
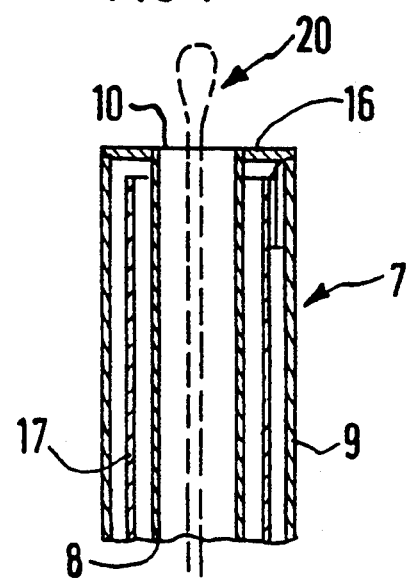

In the embodiment of FIGS. 5 to 7, sleeve 9 has an end part shaped as the end part of the extractor tube 8 and includes, at its free end, an annular wall 16 to connect the free end of tube 8 by welding, said annular wall being co-planar with the inlet opening 10 into tube 8. Tubular rod 9 additionally comprises, here, in the sleeve 9, an intermediate tubular member 17 which is concentric with respect to the extractor tube 8 and extends, at one end, near plate 16, and at the other end, outside sleeve 13. Rod 9 includes joint seal 15 with connecting part 14 of the extractor tube 8. As seen in FIG. 5, the intermediate tubular member 17 thus defines, in sleeve 9, a back and forth flow trajectory of cooling fluid following two parallel chambers, the inlet 11 of cooling fluid opening in the space between the outer sleeve 9 and the intermediates tube 17, the outlet 12 of cooling fluid opening in the space between the intermediate tubular member 17 and the connecting part 14 of the extractor tube 8. In these embodiments, the tubular rod 9 has a straight cylindrical main part and may therefore be radially engaged in the duct for the extraction of fumes 6, by means of an opening 18 provided in the wall of the latter, the tubular rod being maintained in adjustable position by means of a case 19 fixed on the duct 6 opposite opening 18 and provided with unlockable means (not illustrated) for blocking the tubular rod 9 in position.

In the embodiment of FIG. 6, the elbow shaped free end of the tubular rod consists of an assembly at right angle, which is less costly to produce. In the embodiment of FIG. 7, the tubular rod 9 has no elbow shaped end and is completely straight, the opening 10, enabling access to the extractor tube 8, being perpendicular to the axis of the tubular rod, and consequently, parallel, in mounted position, to the flow of fumes F in duct 6. The arrangement according to FIG. 7 has the advantage of enabling the mounting, in the tubular rod for sampling fumes 7, of a thermocouple 20 centrally extending in the extractor tube 8 and projecting outside the latter in the flow of fumes. On the other hand, according to an aspect of the invention, the design of the tubular rod according to FIGS. 2, 4, 5 and 6 enables, as indicated by the arrows F on FIGS. 2, 3 and 5, to orient the tubular rod in counter-current to the flow of fumes and to draw the latter by largely limiting the introduction of dusts carried by the fumes, in the tubular rod and the associated analyzing device.

Figure 3:
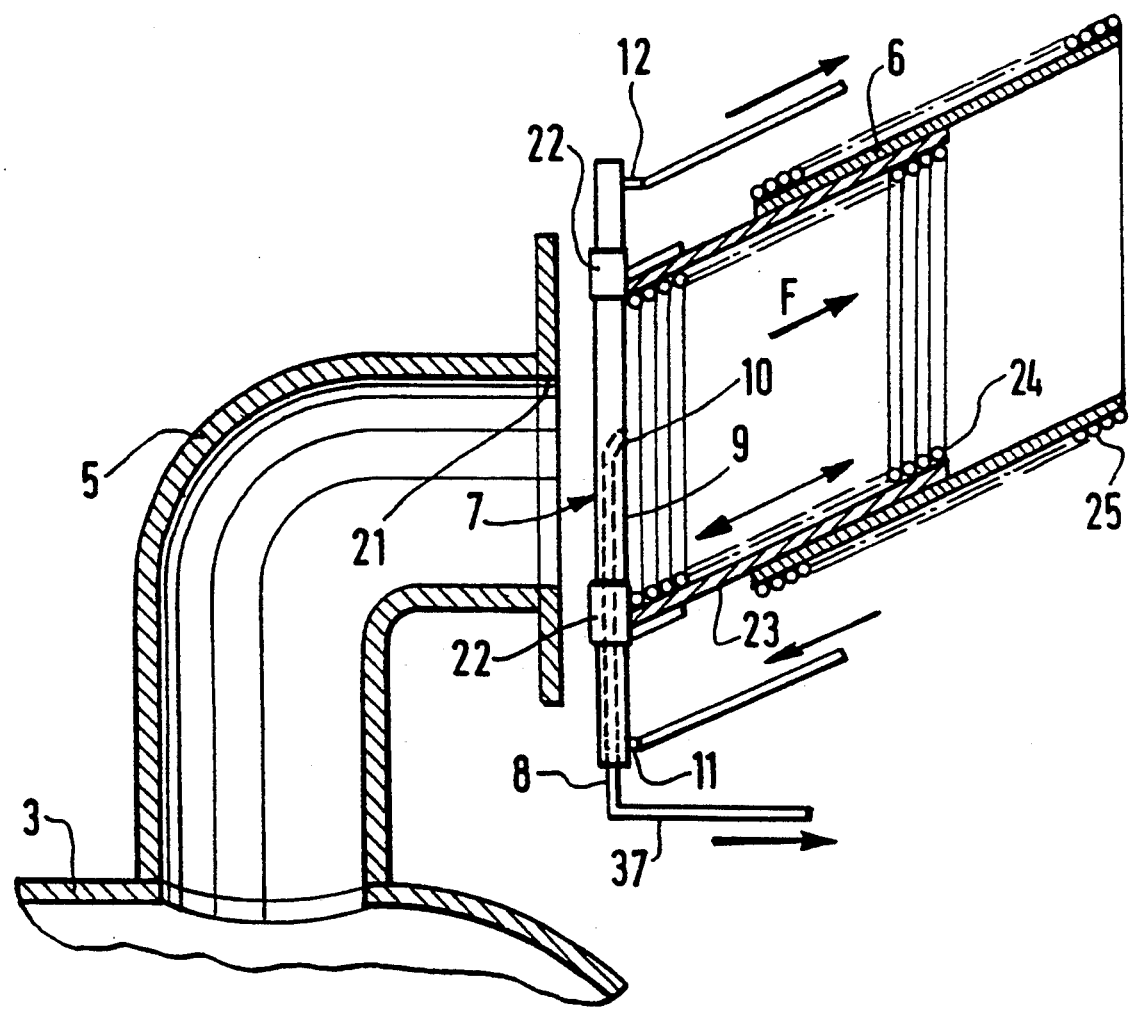
FIG. 3 is a vertical cross-section view of an embodiment for mounting a tubular rod according to FIG. 2, in a system of extracting fumes from a furnace.

FIG. 3 illustrates a particularly advantageous and efficient mounting of a tubular rod according to the embodiment of FIG. 7 in a circuit for the evacuation of fumes from an arc furnace in which the vault 3 and the duct section 5 are movable, typically by rotation around a vertical axis, between a free position, permitting the loading and the unloading of the metal, and an operating position where the outlet end 21 of section 5 is opposite and near the upstream end of the duct for the transfer of fumes 6, an inner space being provided between the two oppositely placed free ends. According to the invention, tubular rod 7 is mounted, by means of two cases 22, on a section of the intermediate tube 23 which is slideably mounted at an end of duct 6. The intermediate section 23 carrying tubular rod 7 is pushed into duct 6 during operations of handling vault 3 of the furnace and, in operating position, the section 23 is out of the tube 6 to bring tubular rod 7 as close as possible to the outlet end 21 of the duct section 5 so that the sampling of the fumes is substantially undisturbed by the extraneous entries of aiis via the residual inner space between sections 5 and 23, which are advantageously provided with cooling coils 24 and 25.

In the various embodiments, the elements which constitute tubular rod 7 are typically made of stainless steel.

The analysis and control part of a device and apparatus according to the invention will now be described with reference to FIGS. 1 and 8.

As seen in FIG. 5, the sampling tubular rod 7 is connected by means of a removable joint enabling the mechanical cleaning, from the outside, of the extractor tube 8, to a tubular member 37 leading, in the illustrated embodiment, to a water condenser 53, then to a double set of filters, 54, 54' to stop possible dusts contained in the sampled fumes, and of drying devices 55, 55', upstream of the pumping group 56 in which the backward flow leads to at least two distinct ducts 57 and 58 leading respectively to an analyzer for carbon monoxide 59 followed by an analyzer for carbon dioxide 60 and an analyzer for hydrogen 63. The analyzers 59 and 60 are calibrated by means of calibration gases (nitrogen, carbon monoxide and carbon dioxide) introduced through a duct 61 opening into duct 57 downstream of a stopping valve. Similarly, the analyzer 63 is calibrated by means of a hydrogenated gas introduced through a duct 64 opening into duct 58 downstream of a stopping valve. The analyzers 59, 60 and 63 are connected, by means of lines 64 and 65 to a central unit for processing data 67 also receiving, through a line 68, a signal indicative of the temperature of the fumes supplied by a temperature probe 69 located in duct 6 at the same level as the sampling tubular rod 7 (or integrated with the latter, as already seen with respect to FIG. 7). The central unit 67 may also be connected, via line 72, to a device for flow measurement by marking with helium 71, via line 72, connected at the outlet of the discharge of the pumps 56. The central unit 67 controls, via line 70, a regulator device 73 controlling a proportional valve 74 disposed in a duct 50 for feeding lance 51 with oxygen and additionally comprising a flow meter 75 connected to the control device 73 to which it gives a signal of increased flow which is compared to a predetermined given value.

According to an aspect of the invention, at least one duct 80 for introducing gas under pressure to permit the unplugging by blowing of the tubular rod 7 and serving, in certain cases, to protect the latter when it is not in operation, opens in the upstream part of the duct 37, upstream a stopping valve.

Figure 8:
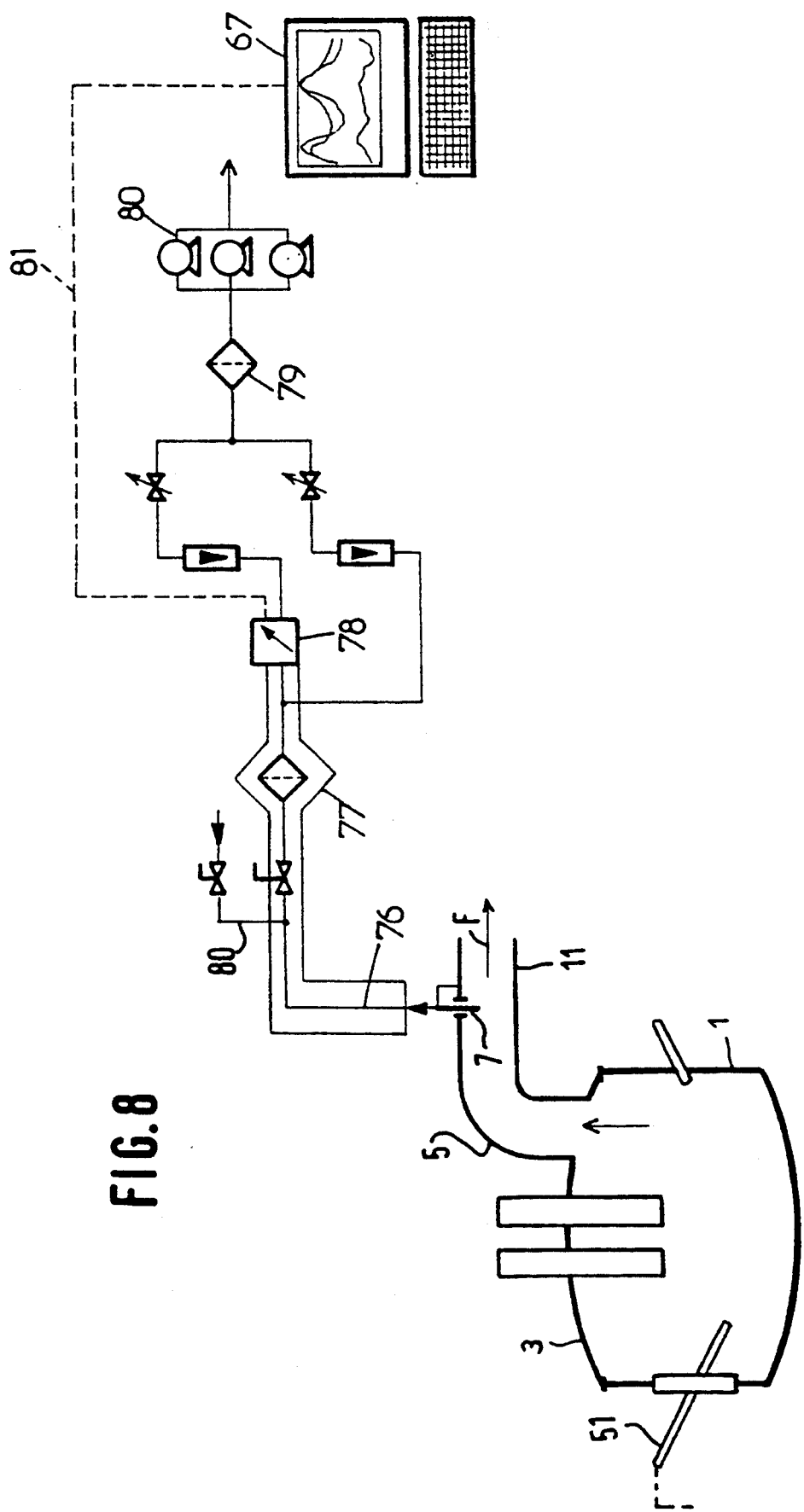
FIG. 8 is a schematic illustration of another embodiment of an apparatus according to the invention.

The above apparatus may be completed, as illustrated in FIG. 8, by an analysis of the water content of the fumes from furnace 1. For this purpose, a sampling tubular rod 7, of the type described previously, disposed in duct 11, is connected, by means of a duct 76 provided with insulating and heating means to prevent any condensation, to a dust filter 77, then to a water analyzer 78, then via a drying zone 79, to a pumping group 80 used for sucking fumes. The value of the water content measured at 78 is transferred through a line 81 towards the unit for processing data 67 in order, in certain cases, to make a compensating correction of the previously made analyses of dry fumes.

Although the present invention has been described with respect to specific embodiments, it is not limited thereto, but on the contrary, modifications and variants which will be obvious to those skilled in the art are possible.

We claim:

1. A fume sampling unit comprising a casing including a main part having an axis and comprising means for connection to a source of a cooling fluid, an extractor tube having an end part extending in the casing and opening outwardly of the casing by a fume inlet opening, and an intermediate tubular member housed in the casing and surrounding the end part of the extractor tube, the intermediate tubular member being spaced from the casing and from the extractor tube to define with the casing and with the extractor tube an inner circuit for the cooling fluid.

2. Device for sampling and analyzing fumes in a duct disposed for the evacuation of fumes, comprising at least one tubular rod mounted on said duct and having a casing including a main part having an axis and comprising means for connection to a source of cooling fluid, an extractor tube having an end part extending in the casing and opening outwardly of the casing by a fume inlet opening and a connection part extending outside the main part of the casing and wherein the fume inlet opening of said extractor tube leads to the trajectory of the fumes inside the duct, and an intermediate tubular member housed in the casing and surrounding the end part of the extractor tube, the intermediate tubular member being spaced from the casing and from the extractor tube to define with the casing and with the extractor tube an inner circuit for the cooling fluid.

3. Apparatus for the production of steel or ferroalloys comprising an arc furnace provided with a duct for the evacuation of fumes and a device for sampling and analyzing said fumes, said device comprising at least one tubular rod mounted on said duct and having a casing including a main part having an axis and comprising means for connection to a source of cooling fluid, an extractor tube having an end part extending in the casing and opening outwardly of the casing by a fume inlet opening and a connection part extending outside the main part of the casing and wherein the fume inlet opening of said extractor tube leads to the trajectory of the fumes inside the duct, and an intermediate tubular member housed in the casing and surrounding the end part of the extractor tube, the intermediate tubular member being spaced from the casing and from the extractor tube to define with the casing and with the extractor tube an inner circuit for the cooling fluid.

4. Apparatus for the production of steel or ferroalloys comprising an arc furnace having a displaceable vault including a fumes duct section and a fumes exhaust duct having an inlet end, said fumes duct section positioned, in operating the arc furnace, in registration with the inlet end of the fumes exhaust duct defining an intermediary space therebetween, and a fume sampling unit mounted on the inlet end of the fumes exhaust duct and including a tubular casing having a lateral wall and opposite inlet and outlet for a cooling fluid, an extractor tube having an end part extending in the casing and opening outwardly of the lateral wall of the casing by a fume inlet opening, the casing positioned within the intermediary space with the opening of the extractor tube facing the inlet end of the fume exhaust duct.

5. The fume sampling unit according to claim 1 wherein the fume inlet opening is substantially coaxial to the axis of the main part of the casing.

6. The fume sampling unit according to claim 1 wherein the fume inlet opening is substantially perpendicular to the axis of the main part of the casing.

7. The fume sampling unit according to claim 6 wherein the end part of the extractor tube is elbow shaped.

8. The fume sampling unit according to claim 7 wherein the elbow shaped end part has a radius which is three time the diameter of the extractor tube.

9. The fine sampling unit according to claim 7 wherein the casing has an end part shaped as the end part of the extractor tube.

10. Device according to claim 2 wherein the fume inlet opening of said extractor tube is substantially perpendicular to the axis of said main part of said casing, and wherein the tubular rod is oriented in the duct so that the fume inlet opening of the extractor tube is counter-current to the direction of circulation of the fumes.

11. Device according to claim 10 wherein at least one suction means is connected to the extractor tube of the tubular rod and to a system of analysis.

12. Device according to claim 11 wherein the system of analysis comprises a water analyzer.

13. Device according to claim wherein the tubular rod is connected to the water analyzer by means of a circuit including insulation and heating means.

14. Device according to claim 11 and further comprising means for injecting an unplugging gas in the extractor tube of the tubular rod.

15. Device according to claim 11 wherein at least one temperature probe in the trajectory of the fumes is coupled to the system of analysis.

16. Device according to claim 15 wherein the temperature probe extends in the extractor tube of the tubular rod.

17. Apparatus according to claim 3, including at least one suction means connected to the extractor tube and to an analysis system, means for injecting oxygenated gas in the furnace, and adjustable means for feeding oxygenated gas coupled to the analysis system.

18. Apparatus according to claim 3 wherein the arc furnace includes a movable vault provided with a fumes duct section which is placed, in operating position, opposite and near a duct for the transfer of fumes, the tubular rod being disposed in the inner space between the opposite ends of the fumes duct section and of the transfer duct.

19. The apparatus of claim 4, further comprising at least an analysis system and at least one suction means connected to the extractor tube and to the analysis system.

20. The apparatus of claim 19, wherein the arc furnace comprises at least one gas injector and further comprising gas regulating means operatively coupled to the analysis system for selectively supplying at least one gas to the gas injector.

21. The apparatus of claim 20, further comprising a source of oxygen-rich gas for supplying the gas injector via the gas regulating means.

* * * * *

UNITED STATES PATENT AND TRADEMARK OFFICE
CERTIFICATE OF CORRECTION

PATENT NO. : 5,344,122

DATED : September 6, 1994

INVENTOR(S) : Jean-Claude Vuillermoz et al.

It is certified that error appears in the above-identified patent and that said Letters Patent is hereby corrected as shown below:

Claim 13, line 1, (column 6, line 31), after "claim" insert —-12—-.

Signed and Sealed this

Eighth Day of November, 1994

Attest:

BRUCE LEHMAN

Attesting Officer

Commissioner of Patents and Trademarks